United States Patent
Fritzler

(10) Patent No.: US 10,546,713 B2
(45) Date of Patent: Jan. 28, 2020

(54) THERMIONIC EMISSION DEVICE, FOCUS HEAD, X-RAY TUBE AND X-RAY EMITTER

(71) Applicant: SIEMENS HEALTHCARE GMBH, Erlangen (DE)

(72) Inventor: Anja Fritzler, Roettenbach (DE)

(73) Assignee: Siemens Healthcare GmbH, Erlangen (DE)

(*) Notice: Subject to any disclaimer, the term of this patent is extended or adjusted under 35 U.S.C. 154(b) by 253 days.

(21) Appl. No.: 15/679,330

(22) Filed: Aug. 17, 2017

(65) Prior Publication Data

US 2018/0053622 A1 Feb. 22, 2018

(30) Foreign Application Priority Data

Aug. 17, 2016 (DE) .................. 10 2016 215 378

(51) Int. Cl.
| | |
|---|---|
| H01J 35/10 | (2006.01) |
| A61B 6/00 | (2006.01) |
| H05G 1/10 | (2006.01) |
| H01J 35/06 | (2006.01) |
| H01J 35/14 | (2006.01) |

(52) U.S. Cl.
CPC .............. *H01J 35/105* (2013.01); *A61B 6/40* (2013.01); *H01J 35/06* (2013.01); *H01J 35/065* (2013.01); *H01J 35/14* (2013.01); *H05G 1/10* (2013.01); *H01J 2235/06* (2013.01)

(58) Field of Classification Search
CPC .......... H01J 35/105; H01J 35/14; H01J 35/06; H01J 35/065
See application file for complete search history.

(56) References Cited

U.S. PATENT DOCUMENTS

| | | | | |
|---|---|---|---|---|
| 2,996,643 | A | * | 8/1961 | Johnstone ............... H01J 1/135 313/305 |
| 4,520,494 | A | * | 5/1985 | Arita ....................... H05G 1/32 378/108 |
| 6,456,691 | B2 | | 9/2002 | Takahashi et al. |
| 7,133,495 | B2 | * | 11/2006 | Nakamura ............... H05G 1/10 378/114 |
| 8,227,970 | B2 | | 7/2012 | Freudenberger |
| 8,477,908 | B2 | | 7/2013 | Zou et al. |
| 10,043,632 | B2 | * | 8/2018 | Fritzler ................. H01J 35/06 |

(Continued)

FOREIGN PATENT DOCUMENTS

| | | |
|---|---|---|
| DE | 102009005454 B4 | 2/2011 |
| DE | 102010060484 A1 | 5/2011 |
| DE | 102012209089 A1 | 12/2013 |

*Primary Examiner* — David P Porta
*Assistant Examiner* — Jeremy S Valentiner
(74) *Attorney, Agent, or Firm* — Laurence Greenberg; Werner Stemer; Ralph Locher

(57) ABSTRACT

A thermionic emission device includes an indirectly heatable main emitter with a main emission surface and a connectible heat emitter with a heat emission surface. The heat emission surface is disposed at a predefinable distance from the main emission surface. In the operating state, the main emitter is at a constant main potential and the heat emitter can be switched between at least two heating potentials which differ from one another and which differ from the main potential. Through the use of the thermionic emission device, the radiation load for a patient is reduced in the case of dose-modulated x-ray recordings.

17 Claims, 2 Drawing Sheets

(56) References Cited

U.S. PATENT DOCUMENTS

| | | | |
|---|---|---|---|
| 2007/0041503 A1* | 2/2007 | Lenz | H01J 35/105 378/143 |
| 2007/0064874 A1* | 3/2007 | Lenz | H01J 35/105 378/144 |
| 2009/0103683 A1* | 4/2009 | Hauttmann | H01J 35/06 378/119 |
| 2010/0181942 A1* | 7/2010 | Freudenberger | H01J 1/22 315/326 |
| 2011/0116593 A1* | 5/2011 | Zou | H01J 35/065 378/16 |

* cited by examiner

10,546,713 B2

THERMIONIC EMISSION DEVICE, FOCUS HEAD, X-RAY TUBE AND X-RAY EMITTER

CROSS-REFERENCE TO RELATED APPLICATION

This application claims the priority, under 35 U.S.C. § 119, of German Patent Application DE 10 2016 215 378.1, filed Aug. 17, 2016; the prior application is herewith incorporated by reference in its entirety.

BACKGROUND OF THE INVENTION

Field of the Invention

The invention relates to a thermionic emission device. The invention also relates to a focus head, an x-ray tube and an x-ray emitter.

A thermionic emission device of that type is known from German Patent DE 10 2009 005 454 B4, corresponding to U.S. Pat. No. 8,227,970, for instance, and in an x-ray tube functions as a cathode. The known thermionic emission device includes an indirectly heated main emitter, which is embodied as a flat emitter with an unstructured main emission surface and with a heat emitter which is embodied as a flat emitter with a structured heat emission surface. The main emitter and the heat emitter each have at least two connecting lugs, wherein the main emission surface and the heat emission surface are aligned substantially in parallel with one another. The connecting lugs of the main emitter are aligned substantially at right angles to the main emission surface and do not project in the lateral direction beyond the main emission surface. Through the use of the thermionic emission device described in German Patent DE 10 2009 005 454 B4, corresponding to U.S. Pat. No. 8,227,970, the highest possible focal point quality is achieved using devices which are kept simple in construction, and an unwanted expansion or defocussing of the electron beam is also avoided with high thermal loads.

An unstructured emission surface is understood to mean a flat, substantially homogeneous emission surface without slots or similar recesses. An emission surface which is interrupted by slots, for instance, or has a meander-shaped conductor path, is referred to as structured.

In applications in computed tomography, a dose modulation of the x-ray radiation is typically performed, i.e. the applied radiation dose is changed as a function of the position of the x-ray source in relation to the patient. Since the human body has an approximately oval cross-section, the radiation dose, with respect to the reclining patient, is higher with a horizontal x-ray irradiation than with a vertical x-ray irradiation. In order to carry out the modulation of the x-ray dose, in the known case the heating current, which is also referred to as tube current and which heats the emitter of the x-ray source, is switched off periodically. The electron emission from the emitter and thus the generation of x-ray radiation is terminated by switching off the tube current. However, regardless of the type of emitter, that effect occurs with a time delay.

With conventional emitters, above all with flat emitters, the heating current is interrupted and the thermal energy is discharged through the connecting lugs of the emitter itself by using radiation cooling and heat conduction. The thermal emission of the electrons from the emitter is only then terminated when the temperature of the emitter drops below a specific (material-dependent) threshold value (threshold temperature). The electron emission, which still takes place during the cooling of the emitter, is undesirable with respect to the radiation exposure to the patient.

SUMMARY OF THE INVENTION

It is accordingly an object of the invention to provide a thermionic emission device, a focus head, an x-ray tube and an x-ray emitter, which overcome the hereinafore-mentioned disadvantages of the heretofore-known devices of this general type and which with dose-modulated x-ray recordings once again reduces radiation exposure to a patient.

With the foregoing and other objects in view there is provided, in accordance with the invention, a thermionic emission device, comprising an indirectly heatable main emitter with a main emission surface and a connectible heat emitter with a heat emission surface, wherein the heat emission surface is at a predefinable distance from the main emission surface and in the operating state of the main emitter is at a constant main potential and the heat emitter can be switched between at least two heating potentials which differ from one another and which differ from the main potential.

The thermionic emission device according to the invention includes a heat emitter having a heat emission surface which emits electrons and thus heats the main emitter disposed therebelow. The heat emitter therefore serves as a heat source for the main emitter. The main emitter then emits electrons through its main emission surface. Those electrons correspond to the actual tube current and are responsible for the focal point shape on the anode and thus for the imaging.

In the known case, with a dose-modulated x-ray recording, the heating current is interrupted in relation to the heat emitter, as a result of which the heat emission surface cools down correspondingly. The electron emission from the heat emitter is terminated with a time delay once the material-dependent threshold temperature is exceeded. Due to the missing electron emission from the heat emitter, the main emitter (image emitter) likewise cools down with a time delay. When the material-dependent threshold temperature is not reached, in the case of the main emitter the electron emission is then likewise terminated with a time delay.

With a dose-modulated recording, the heating current to the heat emitter was previously firstly interrupted and with the image emitter the heat source was thus switched off with a time delay. Until the electron emission at the main emitter (image emitter) is terminated, in other words the tube current is reduced to zero, both the first time delay when switching off the heat emission and also the second time delay when subsequently cooling the main emitter, are therefore to be taken into account cumulatively.

In order to accelerate the cooling of the main emitter, according to the invention, the heat emitter is at a heating potential which is more positive than the main potential. This means that the direct post heating of the main emitter is prevented by the heat emitter, since no further electrons are emitted in the direction of the main emitter (image emitter). Instead, electrons are emitted from the main emitter in the direction of the heat emitter. As compared with the previously known thermionic emission devices, this results in a faster cooling of the main emitter. The dose modulation is improved as a result.

Due to the device according to the invention, the effect of post heating is restricted, as a result of which the cooling of the main emitter is accelerated.

The following advantageous embodiments can be realized individually or in combination within the scope of the invention as a function of the application or the field of application of the thermionic emission device.

Therefore, the main emitter can be constructed as a flat emitter and can have an at least partially structured main emission surface and/or an at least partially unstructured main emission surface.

Alternatively, the heat emitter can be constructed as a flat emitter and can have an at least partially structured heat emission surface and/or an at least partially unstructured heat emission surface.

According to a further variant, the main emitter and/or the heat emitter can be constructed as a coil emitter (also referred to as filament).

For special applications, it may be advantageous to embody the heat emitter as a connectible anode.

The thermionic emission device according to the invention or its advantageous embodiments are suitable for installation in a focus head.

Through the use of the thermionic emission device or a focus head equipped therewith, an x-ray tube with a significantly improved dose modulation can easily be produced. Due to the short cooling times when the heat emitter is switched off and the significantly shorter cooling times of the main emitter when the heat emitter is switched off, the radiation exposures are reduced correspondingly and the imaging recording times are shortened.

The invention and its advantageous embodiments can be used independently of the type of anodes disposed in the x-ray tube. The anode can thus be embodied as a fixed anode (stationary anode) or as a rotary anode. The anode can also be part of a rotary piston tube.

The x-ray tubes described above can be installed in the emitter housing of an x-ray emitter without modifications.

Other features which are considered as characteristic for the invention are set forth in the appended claims.

Although the invention is illustrated and described herein as embodied in a thermionic emission device, a focus head, an x-ray tube and an x-ray emitter, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
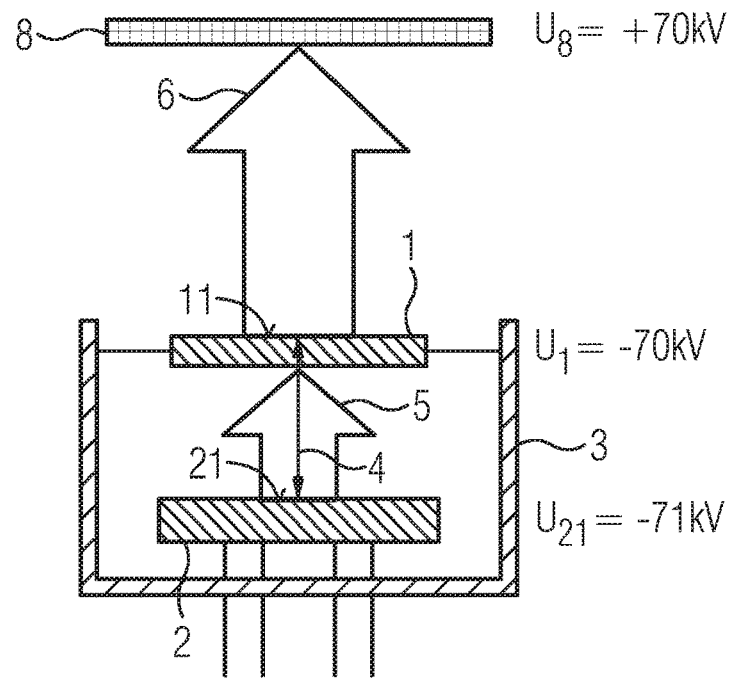
FIG. 1 is a diagrammatic, vertical-sectional view of a first embodiment of a thermionic emission device during normal operation.
Figure 2:
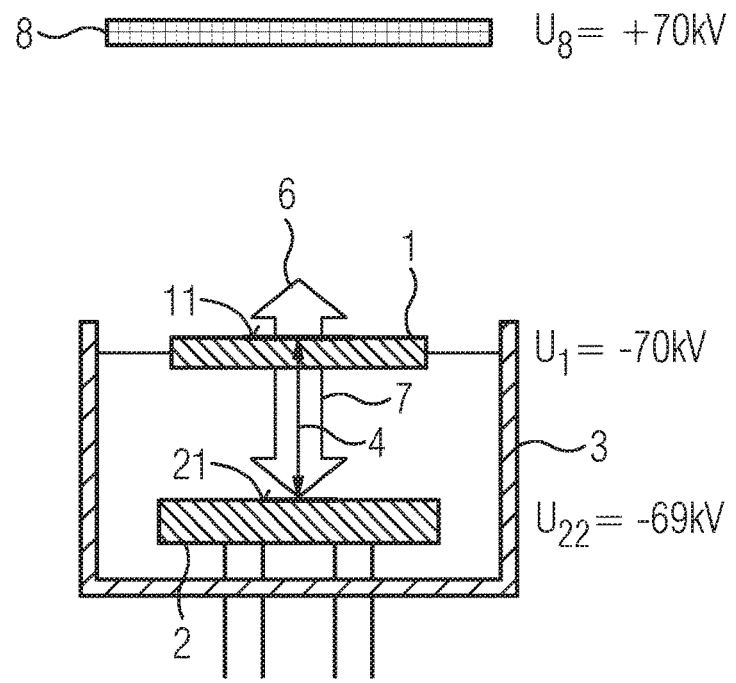
FIG. 2 is a vertical-sectional view showing the thermionic emission device according to FIG. 1 during dose modulation operation.

Referring now in detail to the figures of the drawings and first, particularly, to FIGS. 1 and 2 thereof, there is seen a thermionic emission device in accordance with the invention which includes an indirectly heatable main emitter 1 with a main emission surface 11 and a connectible heat emitter 2 with a heat emission surface 21.

The main emitter 1 and the heat emitter 2 are disposed together in a focus head 3. The main emitter 1 is held mechanically in the focus head 3 and is connected in an electrically conducting manner thereto.

In contrast, the heat emitter 2 is held mechanically in the focus head 3, but is electrically insulated from the focus head 3. The heat emitter 2 can thus be switched independently of the main emitter 1.

Furthermore, the main emitter 1 and the heat emitter 2 are distanced from one another in such a way that the heat emission surface 21 and the main emission surface 11 run at a predefinable distance 4 and substantially in parallel with one another.

In the operating state, the main emitter 1 is at a constant main potential $U_1$ and the heat emitter 2 can be switched between at least two heating potentials $U_{21}$ and $U_{22}$ which differ from one another and which differ from the main potential $U_1$. In the exemplary embodiment shown, the heat emitter 2 can be switched between precisely two different heating potentials $U_{21}$ and $U_{22}$, namely between a first heating potential $U_{21}$ and a second heating potential $U_{22}$.

In the exemplary embodiment shown, the main emitter 1 is at a main potential $U_1=-70$ kV, whereas the heat emitter 2 can be switched between the first heating potential $U_{21}=-71$ kV (FIG. 1) and a second heating potential $U_{22}=-69$ kV (FIG. 2).

During normal operation (FIG. 1), the first heating potential $U_{21}$ is thus more negative than the main potential $U_1$ ($U_{21}<U_1$). During normal operation electrons which are focused on an electron beam 5 by the focus head 3 are thus emitted by the heat emitter 2. The electron beam 5 strikes the main emitter 1 and heats up the main emitter 1. The main emitter 1 emits electrons from the main emission surface 11. Those electrons are focused on an electron beam 6 and are accelerated in the direction of an anode 8. When the electron beam 6 strikes, x-ray radiation is generated in a known manner in the material of the anode 8.

With a dose modulation (FIG. 2), the second heating potential $U_{22}$ is more positive than the main potential $U_1$ and the main potential $U_1$ is in turn more positive than the first heating potential $U_{21}$ ($U_{22}>U_1>U_{21}$). During dose modulation operation, no more electrons are emitted from the heat emission surface 21 of the heat emitter 2 due to a potential assignment which is modified compared with normal operation. Instead, electrons which are focused on an electron beam 7 are additionally emitted from the main emitter 1 in the direction of the heat emitter 2 and strike the heat emission surface 21 there. The main emitter 1 thus emits significantly fewer electrons across its main emission surface 11, so that the electron beam 6 is accordingly weaker and the anode 8 is thus not reached. No x-ray radiation is therefore generated in the material of the anode 8. The potential assignment during dose modulation operation thus reliably counteracts a post heating of the main emitter 1 by the heat emitter 2.

Figure 3:
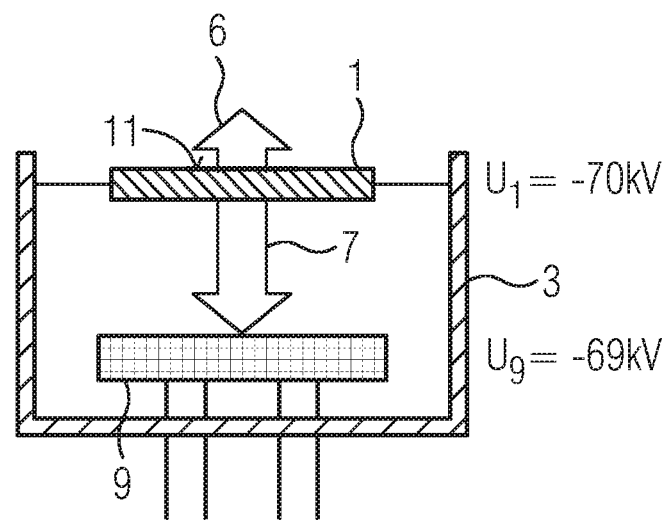
FIG. 3 is a vertical-sectional view showing a second embodiment of a thermionic emission device during dose modulation operation.

The inventive measure can also be transferred to conventional emitter technologies (FIG. 3). To this end, in addition to the main emitter 1 provision is only to be made for a connectible anode 9, which is at an anode potential of $U_9=-69$ kV for instance which corresponds to the second heating potential $U_{22}$ (FIG. 2). During dose modulation operation, the main emitter 1 is thus cooled in the manner described with regard to FIG. 2.

This takes place in such a way that the electrons which are focused on the electron beam 7 are additionally emitted from the main emitter 1, in the direction of the connectible anode 9 and strike there. The main emitter 1 thus emits significantly fewer electrons across its main emission surface 11, so that the electron beam 6 is accordingly weaker and the anode 8 is thus not reached. No x-ray radiation is therefore generated in the material of the anode 8. The potential assignment during dose modulation operation thus reliably shortens the cooling phase of the main emitter 1 with a conventional thermionic emission device.

Although the invention has been illustrated and described in detail on the basis of the preferred exemplary embodiment, the invention is not limited by the disclosed examples and other variants can be derived in this case therefrom by the person skilled in the art without departing from the scope of protection of the invention.

The invention claimed is:

1. A thermionic emission device, comprising:
   an indirectly heatable main emitter having a side with a main emission surface and having an opposite side with a further emission surface; and
   a connectible heat emitter having a heat emission surface;
   said heat emission surface being disposed at a predefinable distance from said main emission surface;
   said main emitter configured to be at a constant main potential;
   said heat emitter configured to be switchable between at least a first heating potential being more negative than the main potential during normal operation and a second heating potential being more positive than the main potential during dose modulation operation.

2. The thermionic emission device according to claim 1, wherein said main emitter is a flat emitter and said main emission surface is formed with slots or has a meander-shaped conductor path.

3. The thermionic emission device according to claim 1, wherein said main emitter is a flat emitter and said main emission surface does not have slots or recesses.

4. The thermionic emission device according to claim 1, wherein said heat emitter is a flat emitter and said heat emission surface is formed with slots or has a meander-shaped conductor path.

5. The thermionic emission device according to claim 1, wherein said heat emitter is a flat emitter and said heat emission surface does not have slots or recesses.

6. The thermionic emission device according to claim 1, wherein said main emitter is a coil emitter.

7. The thermionic emission device according to claim 1, wherein said heat emitter is a coil emitter.

8. The thermionic emission device according to claim 1, wherein said heat emitter is an anode.

9. A focus head, comprising a thermionic emission device according to claim 1.

10. An x-ray tube, comprising:
    an anode; and
    a thermionic emission device according to claim 1.

11. An x-ray tube, comprising:
    an anode; and
    a focus head including a thermionic emission device according to claim 1.

12. The x-ray tube according to claim 10, wherein said thermionic emission device includes an anode.

13. The x-ray tube according to claim 11, wherein said focus head includes an anode.

14. The x-ray tube according to claim 10, wherein said anode is a rotary anode.

15. The x-ray tube according to claim 10, wherein said anode is part of a rotary piston tube.

16. The x-ray tube according to claim 10, wherein said anode is a stationary anode.

17. An x-ray emitter, comprising:
    an emitter housing; and
    an x-ray tube disposed in said emitter housing, said x-ray tube including an anode and a thermionic emission device according to claim 1.

* * * * *